US009259332B2

(12) United States Patent
Danzig et al.

(10) Patent No.: US 9,259,332 B2

(45) Date of Patent: *Feb. 16, 2016

(54) PROSTHETIC VACUUM SYSTEM

(75) Inventors: Morris J Danzig, Lincolnshire, IL (US); Harry David Bush, Palatine, IL (US); Donald Ray McKinney, Gurnee, IL (US)

(73) Assignee: Lincolnshire Manufacturing, LLC, Gurnee, IL (US)

(*) Notice: Subject to any disclaimer, the term of this patent is extended or adjusted under 35 U.S.C. 154(b) by 747 days.

This patent is subject to a terminal disclaimer.

(21) Appl. No.: 11/640,150

(22) Filed: Dec. 14, 2006

(65) Prior Publication Data

US 2008/0147202 A1 Jun. 19, 2008

(51) Int. Cl.

| | |
|---|---|
| ***A61F 2/70*** | (2006.01) |
| ***A61F 2/74*** | (2006.01) |
| ***A61F 2/80*** | (2006.01) |
| ***A61F 2/68*** | (2006.01) |
| ***A61F 2/78*** | (2006.01) |
| *A61F 2/50* | (2006.01) |
| *A61F 2/66* | (2006.01) |
| *A61F 2/76* | (2006.01) |

(52) U.S. Cl.

CPC ... *A61F 2/68* (2013.01); *A61F 2/78* (2013.01); *A61F 2002/5001* (2013.01); *A61F 2002/6614* (2013.01); *A61F 2002/701* (2013.01); *A61F 2002/704* (2013.01); *A61F 2002/742* (2013.01); *A61F 2002/747* (2013.01); *A61F 2002/768* (2013.01); *A61F 2002/7635* (2013.01); *A61F 2002/7655* (2013.01); *A61F 2002/802* (2013.01); *A61F 2002/807* (2013.01)

(58) Field of Classification Search

USPC ........................................................... 623/26

See application file for complete search history.

(56) References Cited

U.S. PATENT DOCUMENTS

| | | | | |
|---|---|---|---|---|
| 2,686,532 | A * | 8/1954 | Hard Af Segerstad | 137/500 |
| 3,671,980 | A | 6/1972 | Baird | |
| 3,922,727 | A | 12/1975 | Bianco | |
| 4,911,724 | A | 3/1990 | Fikes | |
| 5,702,489 | A * | 12/1997 | Slemker | 623/34 |
| 5,735,906 | A | 4/1998 | Caspers | |
| 5,904,722 | A | 5/1999 | Caspers | |
| 6,470,552 | B1 * | 10/2002 | Slemker et al. | 29/447 |
| 6,508,842 | B1 | 1/2003 | Caspers | |
| 6,554,868 | B1 | 4/2003 | Caspers | |
| 6,585,774 | B2 | 7/2003 | Dean, Jr. et al. | |

(Continued)

FOREIGN PATENT DOCUMENTS

DE 003239959 * 5/1984

OTHER PUBLICATIONS

National Aeronautics and Space Administration (NASA), Anthropometry and Biomechanics, vol. 1: Section 3 Curator: SF Website Team Content Manager: Rhonda Rose; NASA Official: Antony Jeeverajan, Ph.D. Last Updated: May 7, 2008 2:04 PM.*

*Primary Examiner* — Marcia Watkins

(74) *Attorney, Agent, or Firm* — Bishop Diehl & Lee, Ltd.

(57) ABSTRACT

An improved prosthetic device with a vacuum system for maintaining a negative pressure seal between the socket and the residual limb. The vacuum system includes a vacuum surge chamber which maintains seal vacuum and increases battery life. The system is small, lightweight, and concealable within the prosthetic device so that it neither impedes use of the device nor detracts from a cosmetically accurate limb.

21 Claims, 10 Drawing Sheets

(56) References Cited

U.S. PATENT DOCUMENTS

| | | | | |
|---|---|---|---|---|
| 6,645,253 | B2 * | 11/2003 | Caspers | 623/26 |
| 6,726,726 | B2 | 4/2004 | Caspers | |
| 6,761,742 | B2 | 7/2004 | Caspers | |
| 6,767,370 | B1 | 7/2004 | Mosler et al. | |
| 6,926,742 | B2 | 8/2005 | Caspers | |
| 6,974,484 | B2 | 12/2005 | Caspers | |
| 7,025,792 | B2 * | 4/2006 | Collier | 623/33 |
| 7,427,297 | B2 * | 9/2008 | Patterson et al. | 623/34 |
| 2002/0138153 | A1 * | 9/2002 | Koniuk | 623/24 |
| 2002/0169515 | A1 * | 11/2002 | Graves et al. | 700/118 |
| 2003/0078674 | A1 * | 4/2003 | Phillips | 623/37 |
| 2003/0181990 | A1 | 9/2003 | Phillips | |
| 2004/0260403 | A1 | 12/2004 | Patterson et al. | |
| 2005/0143838 | A1 | 6/2005 | Collier | |
| 2005/0234563 | A1 * | 10/2005 | Phillips | 623/55 |
| 2005/0240282 | A1 | 10/2005 | Rush et al. | |
| 2006/0155385 | A1 * | 7/2006 | Martin | 623/24 |
| 2006/0224247 | A1 * | 10/2006 | Clausen et al. | 623/24 |
| 2006/0282175 | A1 * | 12/2006 | Haines et al. | 623/24 |
| 2007/0055383 | A1 * | 3/2007 | King | 623/34 |
| 2007/0156252 | A1 * | 7/2007 | Jonsson et al. | 623/24 |

* cited by examiner

PROSTHETIC VACUUM SYSTEM

BACKGROUND OF THE INVENTION

The history of artificial limbs begins with very remote times. There is some evidence that the Romans and the Greeks improvised some sort of substitute for the limbs lost in battle and the vicissitudes of life. Herodotus tells us of a prisoner who amputated his own foot in order to free himself from the shackle, after which he escaped and returned to his friends, who made a wooden foot.

The treasure trove that turned up at Capua in 1885 in a tufa tomb is probably the most valuable and indisputable evidence that artificial legs were made in early times. The relic is now on exhibition in the Museum of the Royal College of Surgeons, London. The official catalogue describes it thus: "Roman artificial leg; the artificial limb accurately represents the form of the leg. It is made with pieces of thin bronze, fastened by bronze nails to a wooden core. Two iron bars, having holes at their free ends, are attached to the upper extremity of the bronze. A quadrilateral piece of iron, found near the position of the foot, is thought to have given strength to it. There was no trace of the foot, and the wooden core had nearly crumbled away."

From those early times to about the beginning of the 20th century, little or no advance was made in the art; and, as no evidence exists to prove to the contrary, it is quite reasonable to suppose that for many centuries the manufacture of artificial limbs was one of the lost arts.

In the early part of the 20th century, the Duke of Anglesea, being in need of an artificial leg, and possessing an inventive faculty, suggested to an English instrument maker, what proved to be a very answerable substitute, a decided improvement on the primitive peg of the doughty Peter. The leg received but little improvement until the venturesome Selpho introduced it into this country with some admirable modifications of his own; here it met with American enterprise and began to thrive.

Typically, artificial limbs are held in place by a series of straps or some type of suspension system. Some are suspended with a silicone sleeve that has a shuttle pin that locks in place and is released by releasing the lock. The present invention creates a vacuum to hold the prosthesis which seems weightless because it is held on so tight.

The earliest use of a vacuum to attach an artificial leg was with above the knee amputees using what is known as the suction socket. This uses the same principle as a suction cup where the maximum strength of the force holding the objects together is a function of the atmospheric pressure at the altitude of use. In artificial leg usage the suction or vacuum is reduced by the vapor pressure of the sweat at the internal temperature of the socket. Use of suction sockets on below knee amputees were not initially practical. The next advance in using vacuum was the introduction of the Harmony system which uses a mechanical vacuum pump operated by the energy of walking. Each step operates the pump.

A mechanical vacuum system improves attachment prevents and eliminates pumping, bruising and increases comfort between the device and the residual limb. A vacuum pump forces out air through a one-way valve, creating negative pressure with every step the patient takes. A tiny tube connects the pump to a weight-bearing socket which is enveloped in a urethane liner or sleeve. By improving attachment, the prosthesis offers better control and equalized pressure on the limb and liner. The pump is powered by the wearer's walking energy. Taking a step compresses the device, which creates the vacuum between the liner and the socket.

The disadvantages of this system are size and weight. There are many amputees that cannot use this system because of size, age, length of the stump and of course children. Replacing the mechanical pump with a small, light, electronically controlled battery driven one, is a solution that is on the market called the Smith system. The Smith system employs a battery driven pump which is electronically controlled. The entire system is in a large box that is strapped to the artificial limb, it lacks a surge chamber and is too large to be cosmetically acceptable. The disadvantages of the Smith system include short battery life because of the constant need to regain an acceptable vacuum level. Other disadvantages are addressed by the advantages described hereinafter which include a surge chamber incorporated as an integral part of the system, and the ability to incorporate the other components in or on the limb and allow it to be made cosmetically acceptable to women, men, and children.

The instant invention provides an improved vacuum system for a prosthetic device using a vacuum source which is connected to the socket cavity thereby drawing the residual limb and liner into firm and total contact with the socket, in which a surge chamber allows the vacuum between the residual limb and the prosthetic device to be sustained for longer periods of time, thus reducing substantially the drain on the battery source and providing longer periods of time between pumping. This system may include a sealable container for a battery, a vacuum pump, and a controller in the form of a circuit board with pressure sensor. The sealable container may be designed to be inserted into the foot of a prosthesis. A leg pipe disposed between the leg cup and the footing can be used as a surge chamber. The surge chamber is disposed inside said leg pipe. Additionally, the battery, vacuum pump, and circuit board may be disposed inside the leg pipe. Sensors and vacuum connections to the socket of the prosthetic device are provided in accordance with the disclosure and pictures provided.

ADVANTAGES OF THIS INVENTION

Unlike the foregoing devices which teach systems that are difficult, if not impossible, for some amputees to use because of their bulk, the nature of the amputation, or size of the individual, which interferes with and limits a user's capability to use the advantages of a secure attachment of the artificial limb. The current invention provides a lightweight, small and concealable vacuum system that is easier for most amputees to use and less tiring to the user. The aesthetic advantages are apparent. The system can be securely concealed in the prosthetic device, principally in a shoe insert or in the leg pipe itself. This allows the limb to be more attractive and available for all size and age users. Thus, it can be used in the widest range of amputees—both below and above the knee.

The incorporation of a concealable vacuum surge chamber connected to the negative pressure environment in the cavity between the socket of the prosthetic device and the residual limb allows the vacuum to be maintained for longer periods of time, thus reducing vacuum pump cycling, which in turn allows for longer use of the battery before recharging is necessary.

The current invention provides excellent control of vacuum range and no loss of vacuum attachment during long periods of inaction as could happen in mechanical vacuum pump systems, which relies on walking to maintain vacuum.

Preferably, the current invention will have a top vacuum in the range of 25 to 20 in. Hg and a low vacuum of about 18 in. Hg to effectively secure the prosthesis to the residual limb.

The present design is to optimally limit pressure drop to about 4 in. Hg. This also saves on battery life as the main current draw is the start up of the vacuum pump which draws a lot of current.

These together with other objects of the invention, along with the various features of novelty which characterize the invention are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Still other advantages will be apparent from the disclosure that follows.

SUMMARY OF THE INVENTION

According to one aspect of the invention, an improved prosthetic device, having a vacuum system for maintaining a negative pressure in a cavity between a socket of a prosthetic device and a residual limb on which the prosthetic device is attached, is taught. The vacuum system comprises a concealable vacuum surge chamber, a vacuum pump, a power source, tubing, tubing connectors, and means for sensing pressure and actuating the system, in which the cavity is operatively connected to the surge chamber and the vacuum pump with the tubing and tubing connectors and the means for sensing pressure and actuating the system comprises a pressure sensor is operatively associated with one of the cavity and the surge chamber. The sensor triggers an actuation event when the negative pressure decays to a predetermined differential from atmospheric pressure to actuate the vacuum pump to increase the negative pressure in the cavity and another actuation event when the negative pressure reaches a predetermined threshold to de-activate the vacuum pump. The vacuum surge chamber is purposefully concealed in a component of the prosthetic device so that it neither impedes use of the device nor detracts from a cosmetically accurate limb.

According to another aspect of the invention, a system for extending the life of a battery in a prosthetic device in which the battery powers a vacuum pump for maintaining a negative pressure in a cavity between a socket of the prosthetic device and a residual limb on which the prosthetic device is attached, a pressure sensor for sensing pressure and actuating the pump, and a circuit board operatively connected to the pressure sensor, comprising a concealed surge chamber operatively connected to the cavity, said pressure sensor being operatively associated with one of the cavity and the surge chamber, and said vacuum surge chamber is concealed in one of a shoe insert adapted and constructed to be inserted along with a base plate of the prosthetic device into a shoe to be worn by a user and a sealed reservoir in a hollow portion of a leg pipe of a prosthetic device, so that it neither impedes use of the device nor detracts from a cosmetically accurate limb. In this way, an interval of time between the sensor sending signals to the circuit board to activate the vacuum pump when the negative pressure in the surge chamber and cavity decays to a predetermined differential from atmospheric pressure increases so that the drain on the battery is reduced and the life of the battery is extended.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWING

Embodiments of the invention are illustrated by way of example, and not by way of limitation, in the figures of the accompanying drawings and in which like reference numerals refer to similar elements and in which.

DETAILED DESCRIPTION OF THE INVENTION

Figure 1:
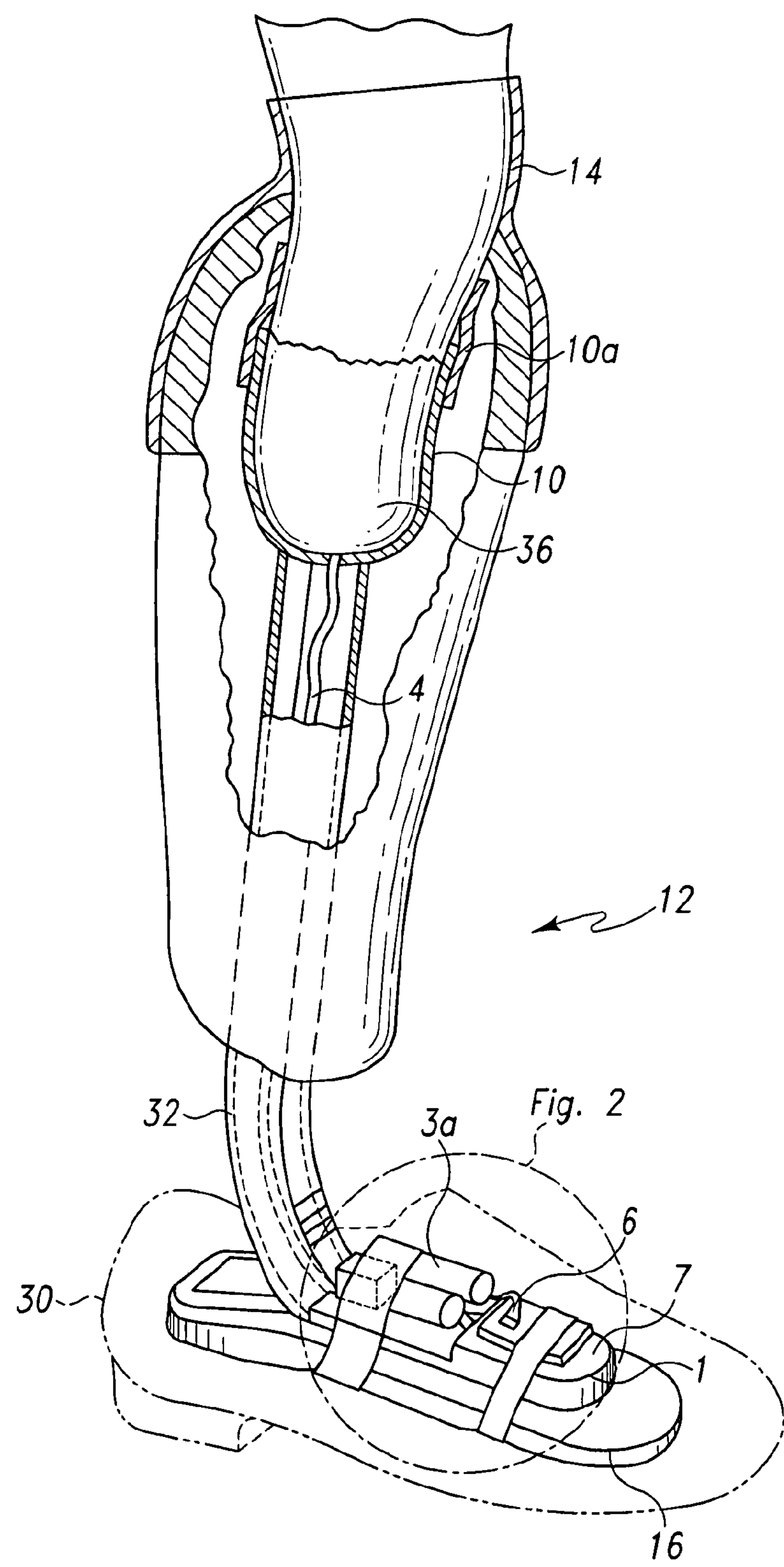
FIG. 1 is a perspective cut away view of a prosthetic device with a vacuum system for maintaining a negative pressure in a cavity between a socket of the prosthetic device and a residual limb showing the battery, vacuum pump and controller including circuit board with an integral pressure sensor mounted on a shoe insert which can be attached to the base plate of the prosthetic device.

In the following description, specific details are set forth in order to provide a thorough understanding of the invention.

However, it will be apparent that the invention may be practiced without these specific details.

Without departing from the generality of the invention disclosed herein and without limiting the scope of the invention, the discussion that follows, will refer to the invention as depicted in the drawing.

According to one embodiment, a vacuum system for maintaining a negative pressure in a cavity 36 between a socket 10 of a prosthetic device 12 and a residual limb 14 on which the prosthetic device is attached. The vacuum system comprises a concealable vacuum surge chamber 1, a vacuum pump 2, a power source 3, tubing 4, tubing connectors 5, and means for sensing pressure and actuating the system, in which the cavity 36 is operatively connected to the surge chamber 1 and the vacuum pump 2 with the tubing 4 and tubing connectors 5 and the means for sensing pressure and actuating the system comprises a pressure sensor 6 is operatively associated with one of the cavity 36 and the surge chamber 1. The vacuum pump is presumed to have an integral check valve to stop back flow from the cavity and a muffler. Alternatively, a one-way check valve could be provided. The sensor triggers an actuation event when the negative pressure decays to a predetermined differential from atmospheric pressure to actuate the vacuum pump 2 to increase the negative pressure in the cavity 36 and another actuation event when the negative pressure reaches a predetermined threshold to de-activate the vacuum pump 2. The vacuum surge chamber 1 is purposefully concealed in a component of the prosthetic device 12 so that it neither impedes use of the device nor detracts from a cosmetically accurate limb. Part of the prosthetic device is a resilient, generally elastic sleeve 10*a* that is used to seal the rim of the socket to the residual limb to allow for a negative pressure to be created in the cavity.

The surge chamber contemplated will have a preferred volume capacity of about 1.5 cubic inches. Surge chambers with a range 1-1.75 cubic inches are expected to meet the requirements of this invention. Obviously, special situations for children with small residual limbs or large adults may cause this range to vary. Typically, the free volume in the socket is small as a preferred design of the socket of a prosthetic device tries to achieve total contact with the limb. Excess socket volume can cause problems. One of the purposes of the surge chamber is to prevent the frequent on-off of the pump and to maintain a good vacuum for tight attachment of the prosthesis. A very small leak without a surge chamber is a large loss of vacuum in the cavity, whereas, a comparable small leak with a surge chamber will not result in a significant loss of vacuum.

In one embodiment of this important invention, the component comprises a shoe insert 7 adapted and constructed to be inserted along with a base plate 16 of the prosthetic device 12 into a shoe 30 to be worn by a user. Preferably, the shoe insert 7 comprises an internal reservoir 9 for the vacuum surge chamber 1. Moreover, the shoe insert may comprise a cover 7*a* for enclosing a space 8, said space and cover being adapted and constructed to receive the vacuum pump 2, power source 3, and the means for sensing pressure and actuating the system, so that the vacuum pump, power source, and the means for sensing pressure and actuating the system can be protected in the enclosed space 8. Alternatively, the vacuum surge chamber 1 may comprise a sealed reservoir 9 in a hollow portion of a leg pipe 32 of a prosthetic device.

The shoe insert 7 can be made from ABS impact system, engineering grade of polyethylene polypropylene. A layer of high density foam, i.e. PVC, silicone, etc., to reduce vibrations from the vacuum pump as well.

Figure 2:
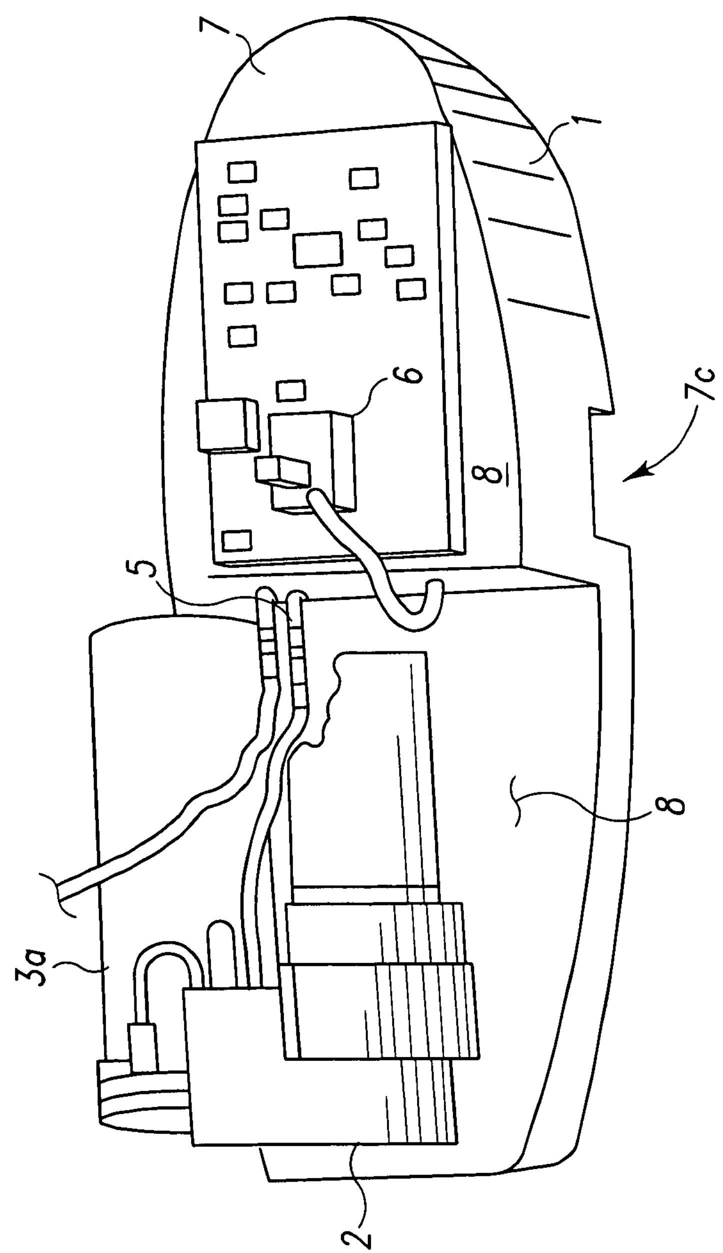
FIG. 2 is an enlarged view showing placement of the pump, battery and circuit board on a top surface of the shoe insert with said shoe insert having a transverse notch on the bottom surface to accommodate base plate bolts that project upwardly as shown in FIG. 6.
Figure 3:
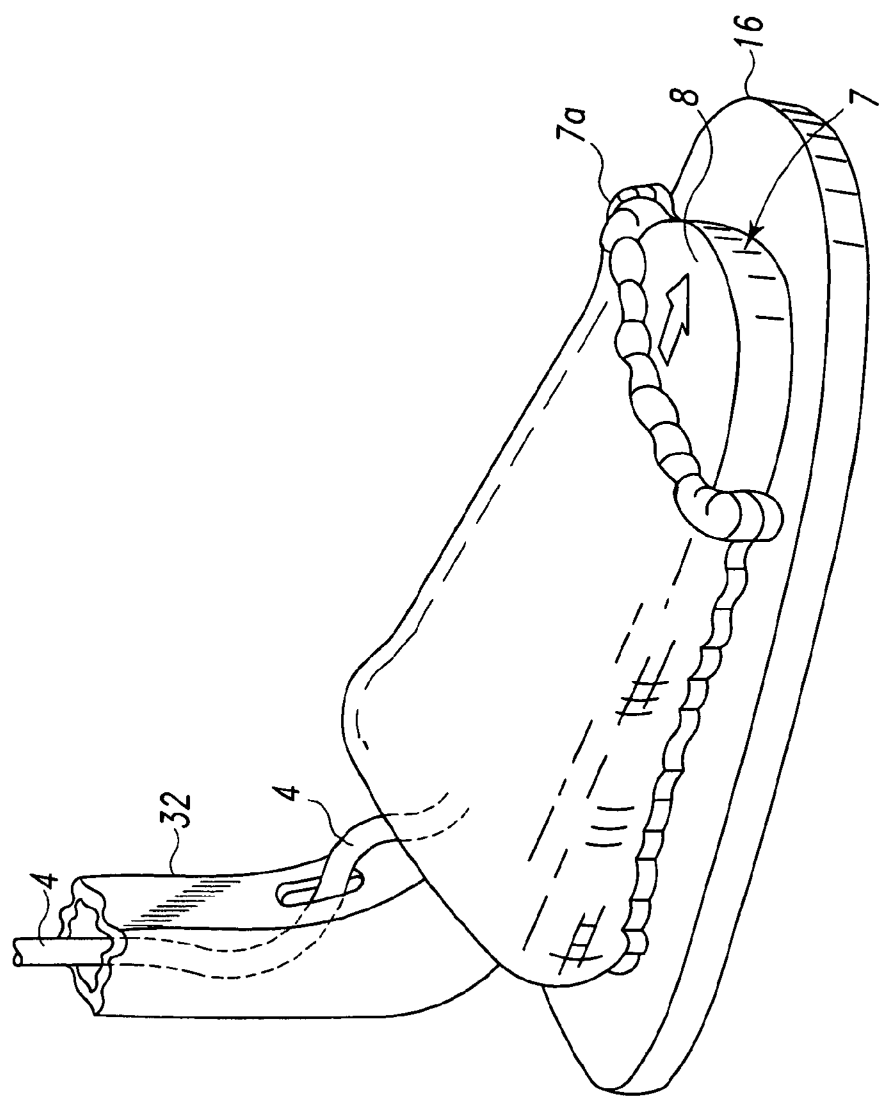
FIG. 3 is a fragmentary perspective view of the shoe insert disposed on the base plate with a cover to enclose the space on the shoe insert on which the battery, vacuum pump and circuit board with an integral pressure sensor components are disposed.
Figure 4:
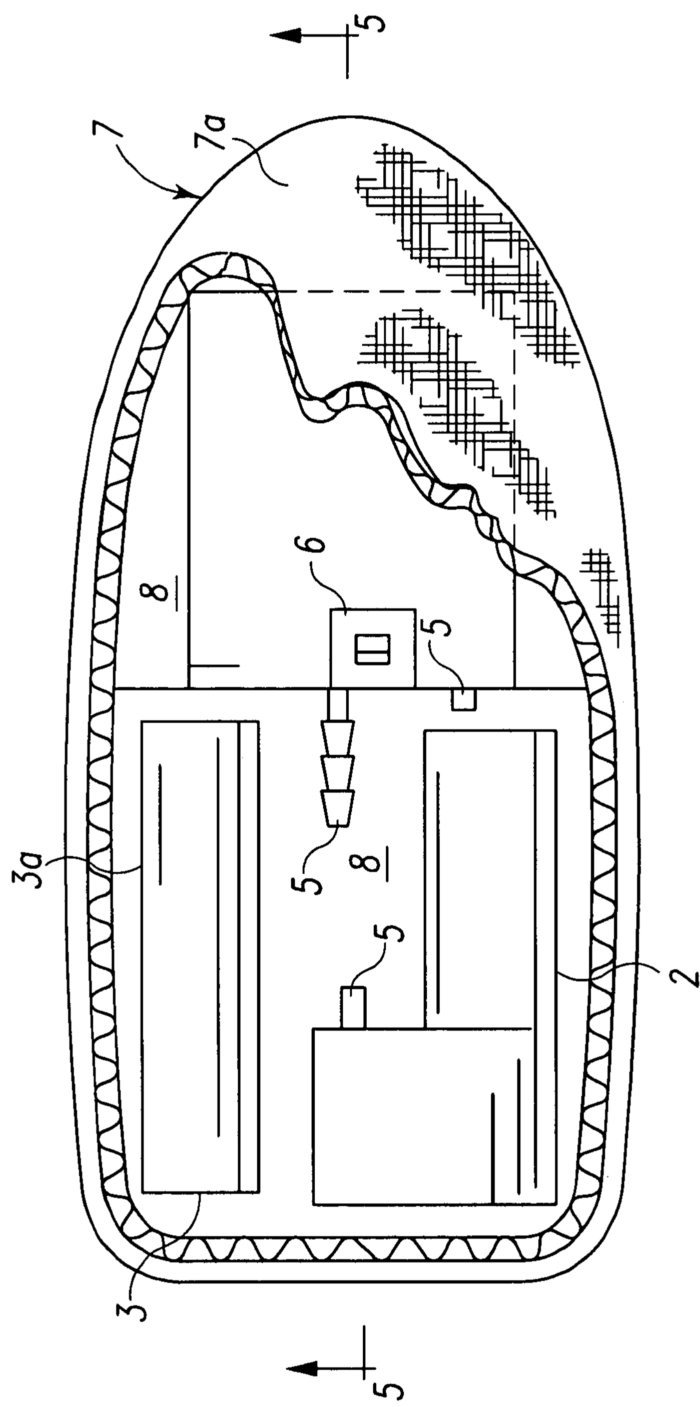
FIG. 4 is a top plan view of the shoe insert with a fragment of the cover being removed to show details of the components arrangement.
Figure 5:
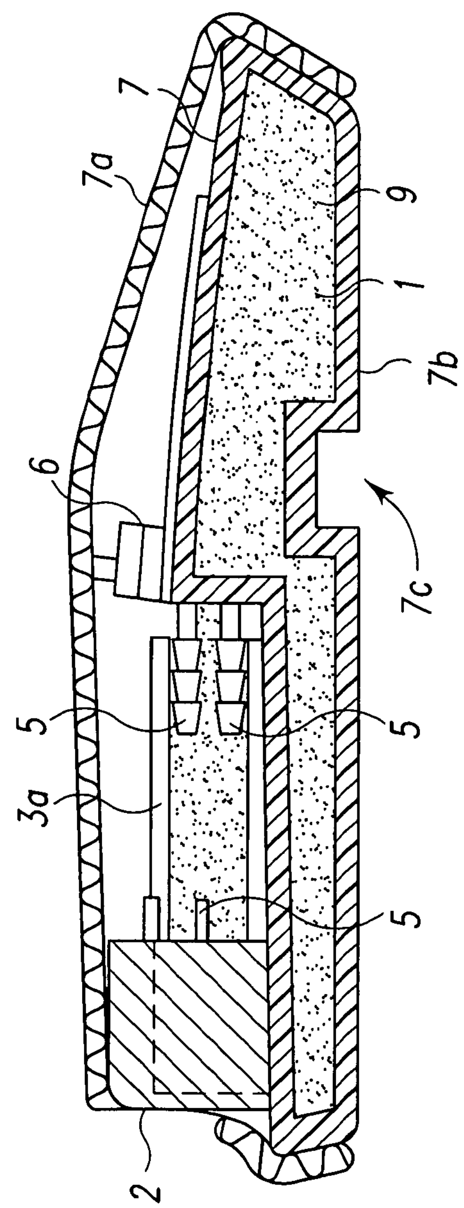
FIG. 5 is a cross sectional view taken along the lines 5-5 of FIG. 4 showing the full cover disposed over the space of the shoe insert and further showing the surge chamber within the body of the shoe insert.
Figure 6:
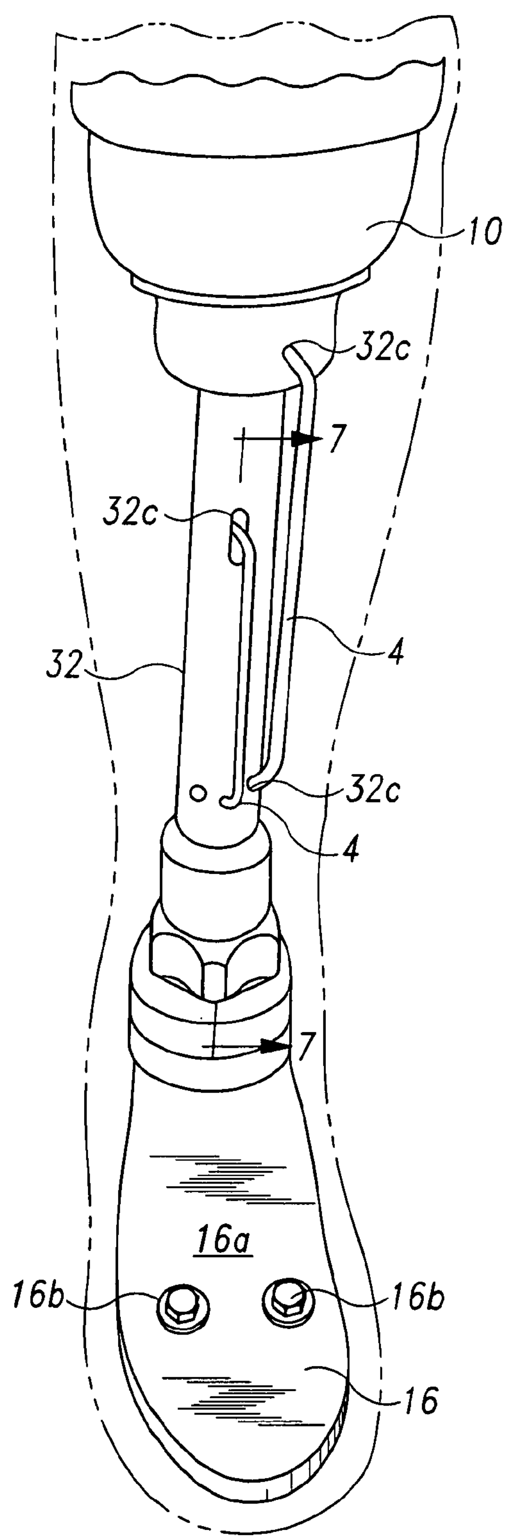
FIG. 6 is a perspective view of another preferred embodiment of a vacuum system for use with a prosthetic device in which the vacuum system components are disposed in the leg pipe.

As best shown in FIG. 1, the shoe insert 7 may be adapted and constructed to be attached to a top surface 16*a* of the base plate 16 of the prosthetic device. Moreover, the shoe insert 7 may have a bottom surface 7*b* with a transverse notch 7*c* suitably sized to receive machine bolts 16*b* disposed on a top surface 16*a* of the base plate, as shown in FIG. 2.

Figure 7:
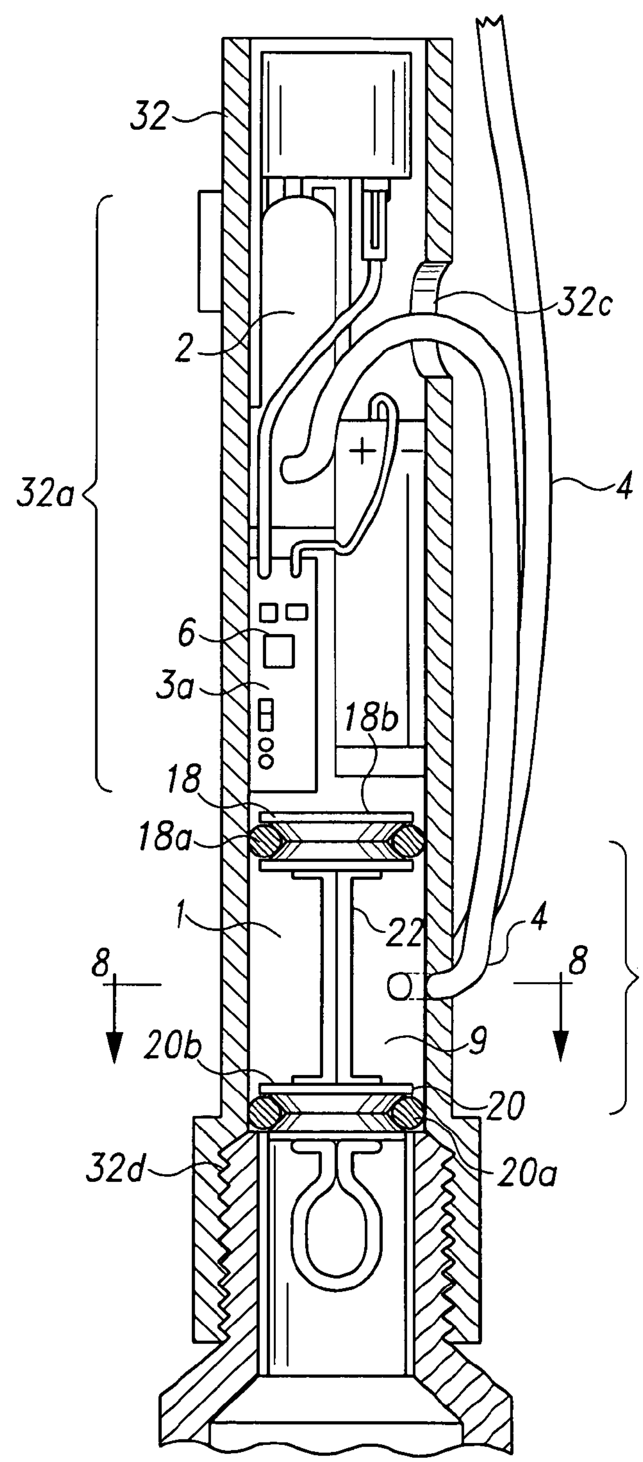
FIG. 7 is a cross sectional view taken along the line 7-7 of FIG. 6 showing the pump, battery and circuit board and a cross sectional view of the surge chamber located in another section of the leg pipe.
Figure 8:
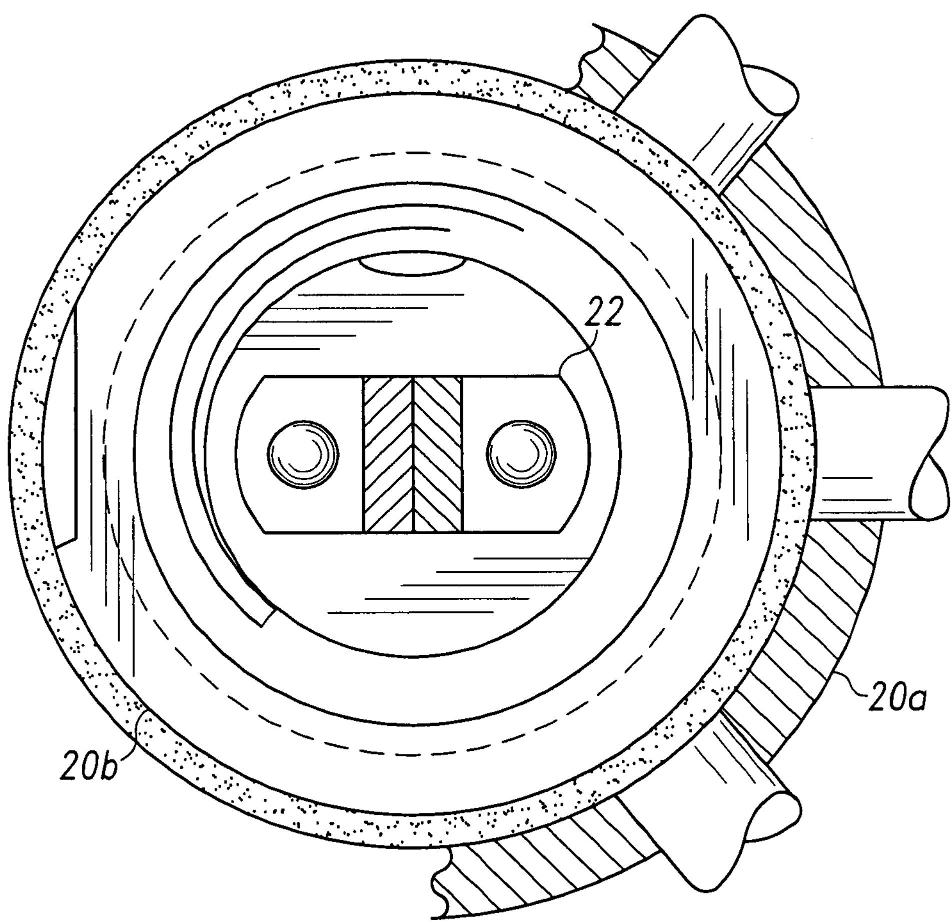
FIG. 8 is a cross sectional view taken along the line 8-8 of FIG. 7 showing a bottom seal arrangement and showing the openings in the leg pipe wall to accommodate the tubing from the pump and a second opening in the pipe wall for the tubing connecting the surge chamber with the socket of the prosthetic device.
Figure 9:
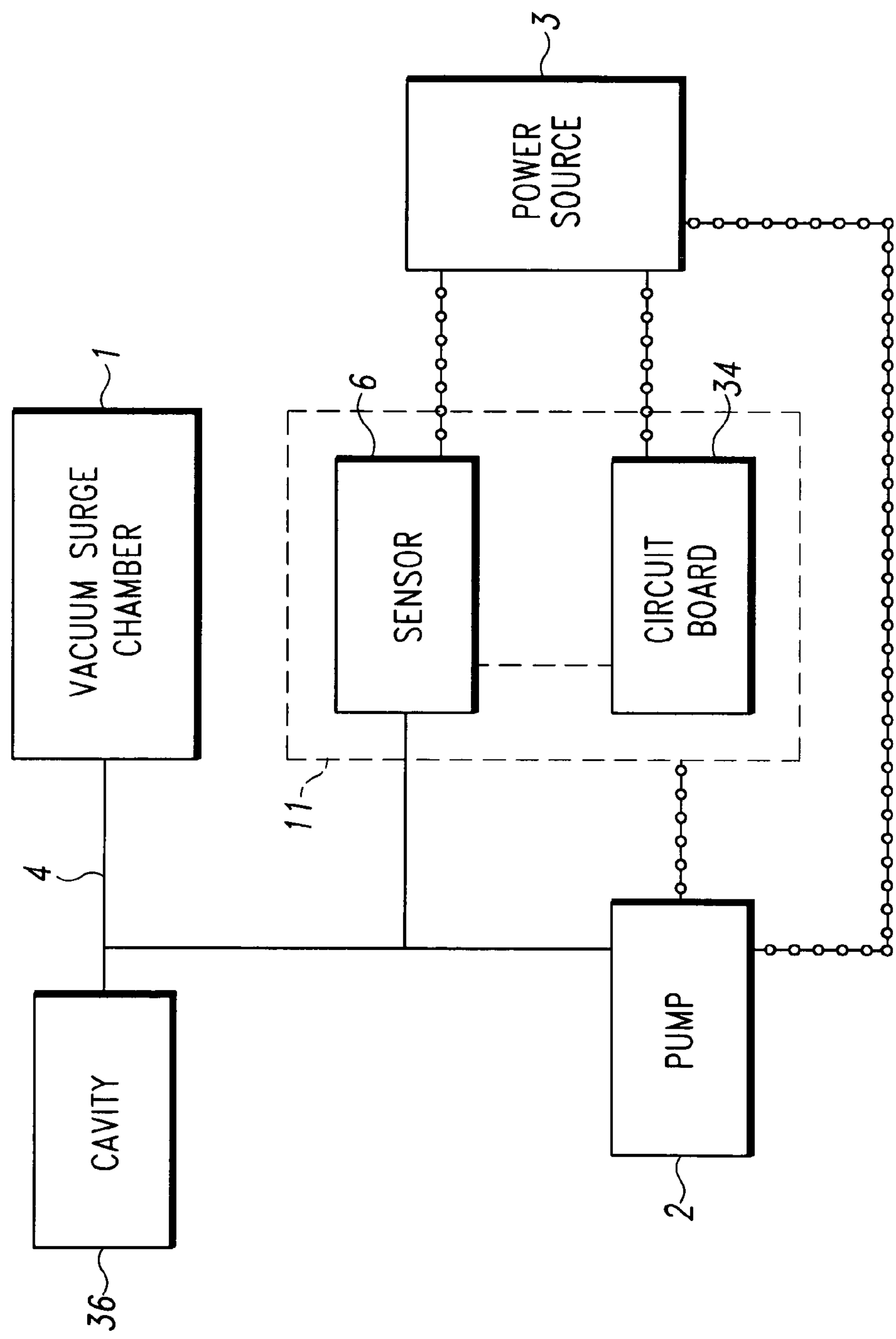
FIG. 9 is a schematic showing the vacuum system tubing connection between the vacuum surge chamber and the pump and the sensor, and the signal connection between the sensor, circuit board and pump, and further showing the sensor, circuit board and pump being electrically powered by the power source.

In one embodiment of the invention shown in FIG. 7, the vacuum surge chamber 1 comprises a sealed reservoir 9 in a hollow portion of a leg pipe 32 of a prosthetic device. Additionally, a hollow portion of the leg pipe 32 may have a first section 32*a* and a second section 32*b*, in the first section the battery 3*a*, pump 2 and means for sensing pressure and actuating the system can be mounted and the first section 32*a* may have an opening 32*c* for receiving a tube 4 and electric switch wiring operatively connected to the cavity, and in the second section 32*b* of the hollow portion of the leg pipe 32 the vacuum surge chamber 1 may be disposed. Furthermore, an end of the second section 32*b* of the hollow portion of the leg pipe may have an end flange with an inner dimension that is less than a parallel inner dimension of the second section creating a inner step 32*d* between the end flange and the second section 32*b*, said inner step is adapted to receive a first seal 18 comprising a first o-ring 18*a* and a first end cap 18*b*, a second seal 20 is provided comprising a second o-ring 20*a* and a second end cap 20*b* which are disposed at a spaced distance from the first o-ring 18*a* and first end cap 18*b* through a longitudinal spacer 22 with the vacuum surge chamber 1 disposed between the first seal 18 and the second seal 20.

A preferred aspect of the invention includes the means for sensing pressure and actuating the system comprises a controller 11 including circuit board 34 and a pressure sensor 6. The circuit board 34 actuates the pump 2 when the pressure sensor 6 detects a loss of negative pressure and sends a signal to the circuit board 34. The power source 3 for supplying power to the circuit board 34, the pump 2, and the sensor 6 may be a Li-ion battery or Li-polymer battery 3*a*.

Figure 10:
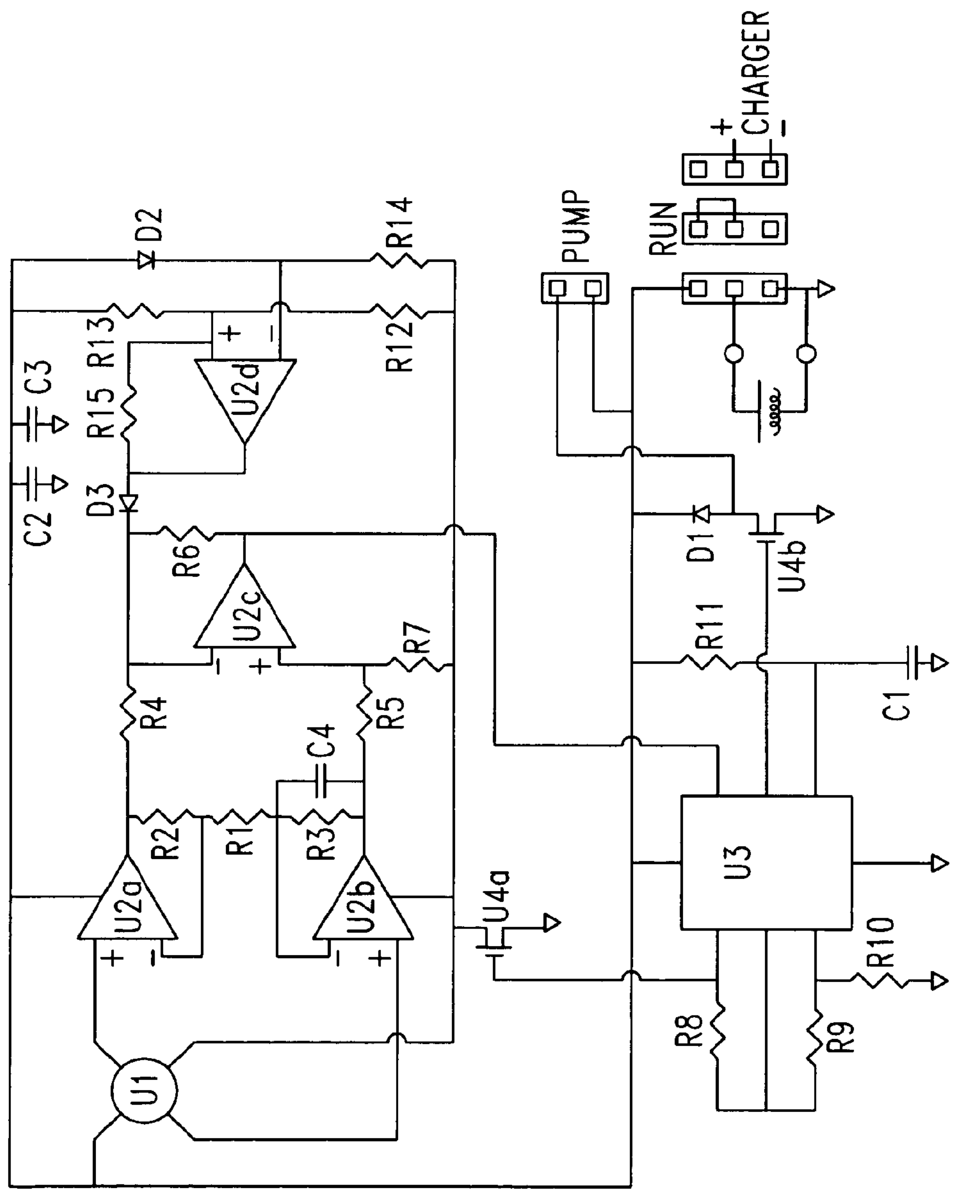
FIG. 10 is a circuit diagram of the controller for the vacuum system.

The controller 11, which includes circuit board 34 and a pressure sensor 6, applies battery power to the vacuum pump whenever the desired vacuum is too low and outside the desired vacuum range is best shown in FIG. 10. A controller for measuring the vacuum and turning the pump on and off should not consume more than a few percent of the pump power for reasonable operation. Therefore, the controller circuitry needs to be very low current. It was found that the pump could produce the desired vacuum in just a few seconds of operation and retain the vacuum for about fifteen minutes. This represents a duty cycle of about 200 to one, and with a current draw of 200 to 300 milliamperes, while pumping, the average current from the battery is just a few milliamperes.

A review of available vacuum measuring components shows a fairly high current consumption, as the sensor presents a resistance of about five thousand ohms. The output from the sensor is just a few tens of millivolts. A gain stage is then required to obtain a large enough output to measure accurately for comparison.

The approach taken was to sample the vacuum just a few times a second as the vacuum changes slowly during operation. The sample duration period is determined by the comparator selected, the LTC 1041, and is about 80 microseconds. The duty cycle is then about 2500 to 5000 to one, with an equivalent reduction in current for the sensor and amplifier. The LTC 1041 includes an RC (R11 and C1) oscillator to determine the sample period. The current for the resistor in the oscillator then becomes the majority of the controller current and is a few microamperes.

A review of the comparator data sheet (LTC1041, Linear Technology Corp.) requires that all voltages be stable within four microseconds. This, then, requires the components to settle within this time. The vacuum sensor was found to easily meet this requirement, as the impedance levels were several kilohms. The amplifier selected, the LTC6242 (Linear Technology Corp.), was found to settle within four microseconds of power application.

The vacuum sensor, U1, (MPXM2102AS Freescale Semiconductor), has an output voltage from the sensor that is the product of the input voltage, the pressure and a constant of calibration. At the desired vacuum and using a single Li-ion cell as the power source, this is about five millivolts, so a gain of about 410 would give a voltage of about one-half supply. Three-fourths of the quad op-amp, U2 (LTC6242), configured as an instrumentation amplifier that ignores the sensor resistance and uses only the sensor output voltage. The amplifier consists of two stages: the first, consisting of U2*a* and U2*b*, amplify the differential output voltage from U1. The gain of this stage is determined by the sum of R1, R2, and R3 divided by the value of R1. With the values shown on the parts list, this value is 26.4. The second stage, U2*c* and resistors R4 through R7, convert the output of the first stage from differential to single ended with a minus supply reference and also supply additional gain, equal to R6 divided by R4, with R4=R5 and R6=R7. The gain is 15.8 for a total gain of about 417. The output voltage U2*c* from the amplifier is compared by U3 (LTC1041) to a voltage derived from a resistor divider network, consisting of R8, R9, and R10. The voltage at the junction of R8 and R9 sets the center of the pressure range while the voltage at the junction of R9 and R10 determines the offset of the turn-on and turn-off pressures from the pressure center. U3 provides the 80 microsecond sample signal to an N-channel MOSFET transistor U4*a* (IRF7311 International Rectifier Corp.), and to the resistor divider which supplies the negative battery connection to the pressure sensor and amplifier, turning them on at the required time.

A comparison is made between the amplified sensor output and the voltage derived from the resistor network, and is held in an internal CMOS logic flip-flop connected to the output pin. This output is supplied to a second MOSFET U4*b*, which supplies battery negative to the load, the pump. The MOSFETs were selected for package size and low resistance. The low resistance eliminates the need for heat sinks and supplies the pump with maximum voltage.

As Li-ion batteries are damaged by over-discharge, the fourth op-amp of U2*d* (LTC6242) was used as a low voltage cutoff. Hysterisis is provided by a resistor R15 from the output to the positive input of the amplifier. The amplifier senses the output of a resistor bridge (R12, R13, and R14) where one leg is replaced by an LED, (660 nm. Agilent Technologies). As the bridge is also turned on only when sampling the sensor, the bridge current is quite low and the LED is not visible, but still provides a reference for the resistor divider sensing the battery voltage. The output of U2*d* goes high when the battery voltage falls to about 3.2 volts. The output is applied through a diode, D3, a 2N2222 transistor selected for its case size, ON Semiconductor, et al.) for isolation during normal operation, to the input of the second stage of the instrumentation amplifier.

The output of the amplifier then falls to a value equivalent to a high vacuum and the comparator turns off the pump load. The circuit continues to operate, pulsing U1, U2 and the resistor network R8 through R10, but the pump remains off until the battery is recharged. D1 (2N2222) is used to protect the switch U4*b* from turn-off transients generated by the inductance of the pump motor. Capacitors C2, C3, and C4 provide stability for the amplifier U2. The three pin connector provides either circuit operation (Run) or a recharging connection for the battery.

The principles of the invention also include a vacuum system for maintaining a negative pressure in a cavity 36 between a socket 10 of a prosthetic device 12 and a residual limb 14 on which the prosthetic device is attached, comprising a vacuum surge chamber, a vacuum pump, a power source, tubing 4, tubing connectors 5, and a circuit board 34operatively connected to a pressure sensor 6 for sensing pressure and actuating the system, in which the cavity 36 is operatively connected to the surge chamber 1 and the vacuum pump 2 with the tubing 4 and tubing connectors 5. The pressure sensor 6 is operatively associated with one of the cavity 36 and the surge chamber 1. The sensor 6 can send a signal to the circuit board when the negative pressure decays to a predetermined differential from atmospheric pressure to actuate the vacuum pump 2 to increase the negative pressure in the cavity, and the sensor 6 can trigger an actuation event when the negative pressure reaches a predetermined threshold to de-activate the vacuum pump. The vacuum surge chamber 1 is preferably concealed in one of a shoe insert 7 adapted and constructed to be inserted along with a base plate 16 of the prosthetic device into a shoe 30 to be worn by a user and a sealed reservoir 9 in a hollow portion of a leg pipe 32 of a prosthetic device, so that it neither impedes use of the device nor detracts from a cosmetically accurate limb.

Moreover, the shoe insert 7 may comprise a cover 7*a* for enclosing a space. The space 8 and cover may be adapted and constructed to receive the vacuum pump, power source, and the circuit board, which may be integral with the sensor 6, so that the vacuum pump, power source, and the circuit board including the sensor 8can be protected in the enclosed space.

Alternatively, the leg pipe 32 may further provide another hollow portion adapted and constructed to receive the vacuum pump, power source, and the circuit board, which may be integral with the sensor 6, so that the vacuum pump, power source, and the circuit board including the sensor can be protected in the leg pipe.

In accordance with the principles of the present invention, a prosthetic device 12 comprising a cosmetically accurate limb extending from a residual limb 14 of a user to a prosthetic foot, a vacuum system for maintaining a negative pressure in a cavity 36 between a socket 10 of a prosthetic device 12 and a residual limb on which the prosthetic device is attached, comprising a vacuum surge chamber, a vacuum pump, a power source, tubing 4, tubing connectors, and a circuit board operatively connected to a pressure sensor 6 for sensing pressure and actuating the system, in which the cavity 36 is operatively connected to the surge chamber and the vacuum pump 2 with the tubing 4 and tubing connectors, the pressure sensor 6 is operatively associated with one of the cavity 36 and the surge chamber. The sensor 6 sends a signal to the circuit board when the negative pressure decays to a predetermined differential from atmospheric pressure to actuate the vacuum pump to increase the negative pressure in the cavity. The sensor 6 also triggers an actuation event when the negative pressure reaches a predetermined threshold to de-activate the vacuum pump. The vacuum surge chamber 1 is concealed in one of a shoe insert 7 adapted and constructed to be inserted along with a base plate 16 of the prosthetic device into a shoe 30 to be worn by a user and a sealed reservoir 9 in a hollow portion of a leg pipe 32 of a prosthetic device, so that it neither impedes use of the device nor detracts from a cosmetically accurate limb.

Additionally, the shoe insert 7 may comprise a cover 7*a* for enclosing a space, said space 8 and cover being adapted and constructed to receive the vacuum pump 2, power source 3, and the circuit board 34, whereby the vacuum pump, power source, and the circuit board can be protected in the enclosed space.

Alternatively, the leg pipe 32 of the prosthetic device 12 may provide another hollow portion adapted and constructed to receive the vacuum pump, power source, and the circuit board, wherein the vacuum pump, power source, and the circuit board can be protected in the leg pipe.

A system for extending the life of a battery 3a in a prosthetic device 12 is also taught by the principles of the present invention in which the battery powers a vacuum pump 2 for maintaining a negative pressure in a cavity 36 between a socket 10 of the prosthetic device and a residual limb on which the prosthetic device is attached, a pressure sensor 6 for sensing pressure and actuating the pump, and a circuit board operatively connected to the pressure sensor, comprising a concealed surge chamber operatively connected to the cavity, to enhance the volume of the negative pressure system, said pressure sensor being operatively associated with one of the cavity 36 and the surge chamber, and said vacuum surge chamber 1 is concealed in one of a shoe insert 7 adapted and constructed to be inserted along with a base plate 16 of the prosthetic device into a shoe to be worn by a user and a sealed reservoir 9 in a hollow portion of a leg pipe 32 of a prosthetic device, so that it neither impedes use of the device nor detracts from a cosmetically accurate limb. In this way, an interval of time between the sensor 6 sending signals to the circuit board 34 to activate the vacuum pump 2 when the negative pressure in the surge chamber and cavity 36 decays to a predetermined differential from atmospheric pressure increases so that the drain on the battery 3*a* is reduced and the life of the battery 3*a* is extended.

While this invention has been described in connection with the best mode presently contemplated by the inventor for carrying out his invention, the preferred embodiments described and shown are for purposes of illustration only, and are not to be construed as constituting any limitations of the invention. Modifications will be obvious to those skilled in the art, and all modifications that do not depart from the spirit of the invention are intended to be included within the scope of the appended claims. Those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention resides not in any one of these features per se, but rather in the particular combinations of some or all of them herein disclosed and claimed and it is distinguished from the prior art in these particular combinations of some or all of its structures for the functions specified.

With respect to the above description then, it is to be realized that the optimum dimensional relationships for the parts of the invention, including variations in size, materials, shape, form, function and manner of operation, assembly and use, and all equivalent relationships to those illustrated in the drawings and described in the specification, that would be deemed readily apparent and obvious to one skilled in the art, are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A vacuum system for maintaining a negative pressure in a cavity between a socket of a prosthetic device and a residual limb on which the prosthetic device is attached, the vacuum system comprising:

a concealable vacuum surge chamber comprised of a sealed reservoir having a volume capacity in the range of about 1.0 to about 1.75 cubic inches, a vacuum pump, a power source, tubing, tubing connectors, and means for sensing pressure and actuating the system, wherein, a. the cavity is operatively connected to the surge chamber and the vacuum pump with the tubing and tubing connectors;

b. the means for sensing pressure and actuating the system comprises a pressure sensor which is operatively associated with one of the cavity and the surge chamber, i. said sensor being capable of triggering an actuation event when the negative pressure decays to a predetermined differential from atmospheric pressure to actuate the vacuum pump to increase the negative pressure in the cavity, ii. said sensor being capable of triggering an actuation event when the negative pressure reaches a predetermined threshold to de-activate the vacuum pump;

c. said vacuum surge chamber being concealed in a component of the prosthetic device so that it neither impedes use of the device nor detracts from a cosmetically accurate limb.

2. The vacuum system of claim 1, wherein the component comprises a shoe insert adapted and constructed to be inserted along with a base plate of the prosthetic device into a shoe to be worn by a user.

3. The vacuum system of claim 2, wherein the shoe insert comprises an internal reservoir for the vacuum surge chamber.

4. The vacuum system of claim 2, wherein the shoe insert comprises a cover for enclosing a space, said space and cover being adapted and constructed to receive the vacuum pump, power source, and the means for sensing pressure and actuating the system, whereby, the vacuum pump, power source, and the means for sensing pressure and actuating the system can be protected in the enclosed space.

5. The vacuum system of claim 2, wherein the shoe insert is adapted and constructed to be attached to a top surface of the base plate of the prosthetic device.

6. The vacuum system of claim 5, wherein the shoe insert has a bottom surface with a transverse notch suitably sized to receive machine bolts disposed on a top surface of the base plate.

7. The vacuum system of claim 1, wherein the means for sensing pressure and actuating the system comprises a circuit board for actuating the pump when the pressure sensor detects a loss of negative pressure and sends a signal to the circuit board.

8. The vacuum system of claim 1, wherein the vacuum surge chamber comprises a sealed reservoir in a hollow portion of a leg pipe of a prosthetic device.

9. The vacuum system of claim 8, wherein a hollow portion of the leg pipe has a first section and a second section, in the first section a battery, pump and means for sensing pressure and actuating the system can be mounted and the first section has an opening for receiving a tube operatively connected to the cavity, and in the second section of the hollow portion of the leg pipe the vacuum surge chamber is disposed.

10. The vacuum system of claim 9, wherein an end of the second section of the hollow portion of the leg pipe has an end flange with an inner dimension that is less than a parallel inner dimension of the second section creating a inner step between the end flange and the second section, said inner step is adapted to receive a first seal comprising a first o-ring and a first end cap, a second seal is provided comprising a second o-ring and a second end cap which are disposed at a spaced distance from the first o-ring and first end cap through a longitudinal spacer with the vacuum surge chamber disposed between the first seal and the second seal.

11. The vacuum system of claim 1, wherein the power source comprises a low voltage Li-ion battery or a Li-polymer battery.

12. The vacuum system of claim 1, wherein the power source comprises a single Li-ion battery or a Li-polymer battery.

13. A vacuum system for maintaining a negative pressure in a cavity between a socket of a prosthetic device and a residual limb on which the prosthetic device is attached, the vacuum system comprising:

a vacuum surge chamber comprising a sealed reservoir having a volume capacity in the range of about 1.0 to about 1.75 cubic inches, a vacuum pump, a power source, tubing and tubing connectors, and a circuit board operatively connected to a pressure sensor for sensing pressure and actuating the system, wherein, a. the cavity is operatively connected to the surge chamber and the vacuum pump with the tubing and tubing connectors;

b. the pressure sensor is operatively associated with one of the cavity and the surge chamber, i. said sensor sends a signal to the circuit board when the negative pressure decays to a predetermined differential from atmospheric pressure to actuate the vacuum pump to increase the negative pressure in the cavity, ii. said sensor triggers an actuation event when the negative pressure reaches a predetermined threshold to de-activate the vacuum pump;

c. said vacuum surge chamber is concealed in one of a shoe insert or in a hollow portion of a leg pipe of a prosthetic device, so that it neither impedes use of the device nor detracts from a cosmetically accurate limb.

14. The vacuum system of claim 13, wherein the shoe insert comprises a cover for enclosing a space, said space and cover being adapted and constructed to receive the vacuum pump, power source, and the circuit board, whereby, the vacuum pump, power source, and the circuit board can be protected in the enclosed space.

15. The vacuum system of claim 13, wherein the leg pipe further provides another hollow portion adapted and constructed to receive the vacuum pump, power source, and the circuit board, whereby, the vacuum pump, power source, and the circuit board can be protected in the leg pipe.

16. A prosthetic device comprising:

a cosmetically accurate limb for extension from a residual limb of a user to a prosthetic foot, a vacuum system for maintaining a negative pressure in a cavity between a socket of a prosthetic device and a residual limb on which the prosthetic device is attached, the vacuum system comprising:

a vacuum surge chamber comprising a sealed reservoir having a volume capacity in the range of about 1.0 to about 1.75 cubic inches, a vacuum pump, a power source, tubing and tubing connectors, and a circuit board operatively connected to a pressure sensor for sensing pressure and actuating the system, wherein, a. the cavity is operatively connected to the surge chamber and the vacuum pump with the tubing and tubing connectors;

b. the pressure sensor is operatively associated with one of the cavity and the surge chamber, i. said sensor sends a signal to the circuit board when the negative pressure decays to a predetermined differential from atmospheric pressure to actuate the vacuum pump to increase the negative pressure in the cavity, ii. said sensor triggers an actuation event when the negative pressure reaches a predetermined threshold to de-activate the vacuum pump;

c. said vacuum surge chamber is concealed in one of a shoe insert in a hollow portion of a leg pipe of a prosthetic device, so that it neither impedes use of the device nor detracts from a cosmetically accurate limb.

17. The prosthetic device of claim 16, wherein the shoe insert comprises a cover for enclosing a space, said space and cover being adapted and constructed to receive the vacuum pump, power source, and the circuit board, whereby, the vacuum pump, power source, and the circuit board can be protected in the enclosed space.

18. The prosthetic device of claim 16, wherein the leg pipe further provides another hollow portion adapted and constructed to receive the vacuum pump, power source, and the circuit board, whereby, the vacuum pump, power source, and the circuit board can be protected in the leg pipe.

19. A prosthetic device comprising:

an artificial limb for extension from a residual limb of a user to a prosthetic foot, a vacuum system for maintaining a negative pressure in a cavity defined between a socket attached to the artificial limb and the residual limb on which the prosthetic device is attached, the vacuum system comprising:

a vacuum surge chamber comprising a sealed reservoir having a volume capacity in the range of about 1.0 to about 1.75 cubic inches, a vacuum pump, a power source, tubing and tubing connectors, and a pressure sensor for sensing pressure within the cavity and actuating the system, wherein the cavity is operatively connected to the surge chamber and the vacuum pump with the tubing and tubing connectors and the sensor triggers an actuation event when a negative pressure in the cavity reaches a predetermined threshold to de-activate the vacuum pump.

20. The prosthetic device of claim 19, wherein the vacuum surge chamber is supported within the artificial limb.

21. The prosthetic device of claim 20, wherein the vacuum surge chamber is supported within the prosthetic foot.

* * * * *